United States Patent [19]

Naipawer et al.

[11] 3,984,573

[45] Oct. 5, 1976

[54] FOODSTUFFS CONTAINING 2-MERCAPTOBENZOIC ACID AND DERIVATIVES THEREOF

[75] Inventors: Richard E. Naipawer, Wallington, N.J.; Michael Ferro, Ann Arbor, Mich.; Leslie Blau, Dumont, N.J.

[73] Assignee: Givaudan Corporation, Clifton, N.J.

[22] Filed: Jan. 6, 1976

[21] Appl. No.: 646,820

[52] U.S. Cl. ............................ 426/3; 426/535
[51] Int. Cl.$^2$ ............................ A23L 1/235
[58] Field of Search ............................ 426/535, 3

[56] References Cited

UNITED STATES PATENTS

| | | | |
|---|---|---|---|
| 3,677,772 | 7/1972 | Mussinan | 426/535 |
| 3,917,870 | 11/1975 | Slangan et al. | 426/535 |

*Primary Examiner*—Joseph M. Golian
*Attorney, Agent, or Firm*—Thomas Cifelli, Jr.

[57] ABSTRACT

Methods for altering the flavor of foodstuffs and flavoring compositions for foodstuffs by including therein 2-mercaptobenzoic acid and derivatives thereof to produce in the foodstuffs and flavoring compositions a Concord grape flavor.

10 Claims, No Drawings

FOODSTUFFS CONTAINING 2-MERCAPTOBENZOIC ACID AND DERIVATIVES THEREOF

BACKGROUND OF THE INVENTION

Considerable efforts have been directed toward finding suitable flavoring agents which are capable of imparting a desired flavor and/or aroma to foodstuffs. Many popular items of commerce such as soft drinks, wines, gelatin products, confectionery products and the like have grape flavors. Good reconstituted and synthetic grape flavors are in demand for such products. Concord grapes have an intense characteristic flavor which is greatly preferred over the flavors of other varieties of grapes. It is especially desirable to have a flavoring material which imparts the characteristic flavor of Concord grapes.

The aroma of methyl anthranilate has been described as reminiscent of Concord grapes (S. Arctander, "Perfume and Flavor Chemicals", 1st ed., Steffin Arctander, Montclair, N.J., 1969, Monograph 1910). It has also been reported (Tressler, D. K., and Joslyn, M. A., "Fruit and Vegetable Juice", 795, Avi Publishing Co., Inc., Westport, Conn., 1961) that, "the aroma of Concord grapes closely resembles that of methyl anthranilate" . . . and that "the methyl anthranilate increased during the ripening of the grape but that the flavor and aroma of Concord grapes is not entirely due to this ester". Methyl anthranilate lacks the bready, meaty natural aroma of Concord grapes. Consequently, most imitation grape flavors based on methyl anthranilate also lack these characteristics and there is a need for flavor components which will impart to such imitation flavors the bready, meaty notes found in the natural flavor.

2-Mercaptobenzoic acid and methods for preparing it have been repoted (Allen, C. H. F., and MacKay D. D., "Organic Synthesis", Coll. Vol. 2, 580, John Wiley & Sons, Inc., New York, 1943). However, its use as a flavor material was heretofore unknown.

SUMMARY OF THE INVENTION

The compounds of this invention have the formula:

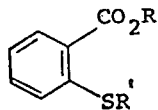

wherein R is hydrogen, an alkali metal or an alkyl group and R' is hydrogen or an alkali metal. It is the surprising and unexpected finding of this invention that these compounds, when used in suitable amounts, are particularly useful in imparting to a foodstuff, or an imitation flavor, highly desirable characteristics of Concord grapes.

DESCRIPTION OF THE PREFERRED EMBODIMENTS

As previously noted, the 2-mercaptobenzoic acid is known. The corresponding esters are also available by methods known in the art. For example, the alkyl esters are quite easily prepared by the classical Fischer esterification involving the heating at reflux of a solution of the 2-mercaptobenzoic acid in the appropriate alcohol of one to four carbon atoms in the presence of an acid catalyst, such as hydrogen chloride, hydrochloric acid, sulfuric acid, p-toluenesulfonic acid and the like. The unreacted 2-mercaptobenzoic acid is washed out by using a dilute aqueous solution of alkali metal hydroxide, such as sodium hydroxide or potassium hydroxide, and may be recovered by acidification of the base wash and recycled. The acid-free ester is vacuum distilled to yield pure alkyl 2-mercaptobenzoate.

The lithium potassium and sodium salts of 2-mercaptobenzoic acid are easily prepared by adding a solution of 2-mercaptobenzoic acid in 1,2-dimethoxyethane (DME) to a stirred suspension of the appropriate alkali metal hydride in DME and evaporating the resultant solution to dryness. Alternately, equal molar amounts of 2-mercaptobenzoic acid and appropriate alkali metal hydroxide are mixed in ethanol solution and the solution evaporated to dryness to yield the alkali metal salt of 2-mercaptobenzoic acid. This latter procedure is preferred on a large industrial scale. The lithium potassium and sodium salts prepared in either of these manners are suitable for imparting a Concord grape flavor to foodstuffs, and are especially suitable in aqueous applications.

In addition to the aforementioned salts of the carboxylic acid group wherein R is an alkali metal, those species wherein the R' group is an alkali metal are also suitable. This would include those compounds wherein R' is an alkali metal and R is an alkyl group. The compound where R' is an alkali metal and R is hydrogen would be expected to quickly revert via exchange of R and R'.

The alkali metal salts of alkyl 2-mercaptobenzoates can be prepared by adding the appropriate ester to a suspension of the alkali metal hydride, preferably sodium hydride, in equimolar amounts and evaporating the solution to dryness. Other methods for preparing these salts may be used but it is to be understood that the particular method used in preparing the compounds is not critical to this invention.

It is a surprising feature of this invention that the esters of 2-mercaptobenzoic acid, the alkali metal salts of these esters (R' =alkali metal), the alkali metal salt of 2-mercaptobenzoic acid (R=alkali metal), and the 2-mercaptobenzoic acid itself have a Concord grape taste with the meaty, bready characteristics desired while certain closely related compounds are devoid of any similar characteristics. If the hydrogen bonded to sulfur is replaced with an alkyl group, the resulting compounds are devoid of any of the taste characteristics of Concord grapes. Such compounds are practically tasteless. Similarly, those analogs wherein the sulfur atom is replaced by oxygen are also devoid of any of the Concord grape characteristics.

In the practice of this invention it is preferred to add to the foodstuff, or to the flavoring composition, a suitable amount of 2-mercaptobenzoic acid or a suitable derivative thereof. Such suitable derivatives include those compounds as previously defined.

It is especially preferred to use 2-mercaptobenzoic acid, the sodium salt of 2-mercaptobenzoic acid wherein R is sodium, the lower alkyl ester of 2-mercaptobenzoic acid wherein R is an alkyl group from one to four carbons and the sodium salts of these esters wherein R' is sodium. All of these compounds impart the bready, meaty Concrod grape character to the foodstuff or imitation flavor. The particular species preferred for a particular application would be based on secondary considerations which would be obvious to the practicing flavorist.

For example, if water solubility were an important secondary consideration, the sodium salts or the lower esters would be preferred in as much as the 2-mercaptobenzoic acid itself has limited solubility in water. Such secondary considerations and preferences would be left to the discretion of the practicing flavorist who, upon the teachings of this invention, would choose among the obvious alternatives such teaching makes available.

To provide the characteristics necessary for a Concord grape flavor, the compounds of this invention should be used in suitable amounts. By suitable amounts we mean herein at levels of between 0.1 ppm to 100 ppm (ppm - parts per million) of the final foodstuff. The compound can be added to the foodstuff directly or as part of an imitation flavor. A suitable amount used to prepared a synthetic flavor would be such that upon use of that flavor the level of compound in the final foodstuff would be as indicated above (0.1 ppm to 100 ppm).

The compounds of this invention are especially suitable for flavoring foodstuffs such as beverages (soft drinks, wines and the like), confections, gelatins, chewing gums and the like.

The following examples are provided to illustrate embodiments of this invention as it is now preferred to practice it. It will be understood that such examples are merely illustrative and the invention is to be limited thereto only as indicated in the claims. Unless otherwise indicated, flavor ingredients are given in parts by weight.

Infrared spectra were recorded as neat samples on a Perkin-Elmer Model 457 spectrophotometer and absorptions are reported as inverse centimeters. Nmr spectra were recorded as solutions in chloroform-d, or dimethyl sulfoxide-$d_6$ on a Varian A-60A spectrometer and are reported as $\delta$ units relative to TMS ($\delta$ 0.0) as an internal standard. Molecular weights were determined from mass spectra on a Perkin-Elmer Model 270 mass spectrometer.

In considering the infrared spectra; (w), (m) and (s) designate weak, medium and strong intensities respectively. In considering nmr spectra; (s), (d), (t) and (q) imply singlet, doublet, triplet and quartet respectively.

EXAMPLE I

In 650 ml of absolute methanol previously saturated with hydrogen chloride gas was dissolved 100 g (0.65 mole) of 2-mercaptobenzoic acid. The solution was stirred at reflux for 2–3 hours, cooled to ambient temperature and the excess methanol removed by distillation at 150 mm. The residual material was cooled. Unreacted 2-mercaptobenzoic acid (14.0 g) crystallized and was recovered by filtration.

The filtrate was dissolved in 150 ml of hexane. This solution was washed twice with 10% sodium carbonate solution and then washed to neutral pH with several water washes. The washed hexane solution was dried over sodium sulfate, filtered and the hexane removed on a rotary evaporator at 20 mm. The residual oil was distilled to yield methyl 2-mercaptobenzoate: 74.6 g (79.6% yield); bp 78°–86°C/0.7 mm; $n_D^{20}$ 1.5940:

ir, 2540 (m), 1710 (s) cm$^{-1}$.

nmr, 3.9$\delta$ (3H, s), 4.8 (1H, s), 6.9–7.3 (3H, complex), 7.8–8.1 (1H, multiplet).

EXAMPLE II

Using a procedure similar to that of Example I, a mixture of 50 g (0.32mole) of 2-mercaptobenzoic acid, 60 g (1.3 moles) of absolute ethanol, 200 ml. of benzene and 1.0 g of sulfuric acid (98%) was heated at reflux for 28 hours and yielded ethyl 2-mercaptobenzoate: 23.3 g (40% yield); bp 99°–100°C/0.8 mm; mol. wt. 182:

ir, no hydroxyl absorption, 1705 (s).

nmr, 1.4$\delta$ (3H, t, J=6Hz), 4.4 (2H, q, J=6Hz), 4.9 (1H, s), 7.0–7.3 (3H, complex), 7.9–8.1 (1H, multiplet).

EXAMPLE III

Using a procedure similar to Example I, a mixture of 50.0 g (0.32 mole) of 2-mercaptobenzoic acid, 60 g (1.0 mole) of anhydrous isopropanol, 200 ml of benzene and 1.0 g of sulfuric acid (98%) was heated at reflux for 22 hours and yielded isopropyl 2-mercaptobenzoate: 13.2 g (20.1% of theory), bp 92°–93°C/0.7 mm.

ir, no hydroxyl absorption, 2520 (m), 1704 (s) cm$^{-1}$.

nmr, 1.4$\delta$ (6H, d, J=6Hz), 4.9 (1H, s), 5.3 (3H, quintet, J=6Hz), 7.0–7.3 (3H, complex), 7.9–8.1 (1H, multiplet).

EXAMPLE IV

A mixture of 50 g (0.32 mole) of 2-mercaptobenzoic acid, 30 g (0.5 mole) of n-propanol, 200 ml of benzene and 1.0 g of sulfuric acid (93%) was stirred at reflux in a flask equipped with a condenser and Dean-Stark water separator. After 24 hours at reflux, 6.0 ml of water was collected in the water separator. The mixture was cooled to ambient temperature, washed with 150 ml of 10% sodium carbonate solution, washed with three 150 ml water washes, dried over sodium sulfate, filtered and concentrated using a rotary evaporator. The residual oil was distilled to give n-propyl 2-mercaptobenzoate: 41.5 g (62% yield); bp 103°C/0.5 mm; mol wt 196:

ir, no hydroxy absorption, 2530 (m), 1705 (s) cm$^{-1}$.

nmr, 1.0$\delta$ (3H, t, J=7Hz), 1.7 (2H, sextet, J=7Hz), 4.3 (2H, t, J=7Hz), 4.8 (1H, s), 7.0–7.4 (3H, complex), 7.9–8.2 (1H, multiplet).

EXAMPLE V

Using a procedure similar to that of Example IV, a mixture of 50 g (0.32 mole) of 2-mercaptobenzoic acid, 50 g (0.7 mole) of n-butanol, 200 ml of benzene and 1.1 g of sulfuric acid (93%) was heated at reflux for 24 hours during which time 5.9 ml of water was collected in the water separator. The mixture was cooled, washed, concentrated and the residual oil distilled to give n-butyl 2-mercaptobenzoate: 46.1 g (68.6% yield); bp 127°–128°C/1.0 mm; mol wt 210:

ir, no hydroxyl absorption, 2520 (m), 1701 (s) cm$^{-1}$.

nmr, 0.9$\delta$ (3H, t, J=6Hz), 1.1–2.0 (4H, complex), 4.3 (2H, t, J=6Hz), 4.9 (1H, s), 7.0–7.4 (3H, complex), 7.9–8.2 (1H, multiplet).

EXAMPLE VI

A solution of 2-mercaptobenzoic acid (15.4 g, 0.1 mole) in 50 ml of 1,2-dimethoxyethane (DME) was slowly added, with cooling, to a stirred suspension of 0.1 mole of sodium hydride in DME, the suspension having been prepared by washing 4.2 grams of a 57% oil dispersion with dry n-hexane (3 times) and replacing the last wash with dry 1,2-dimethoxyethane (50 ml). Cooling was necessary to maintain the temperature below 25°C. The resultant suspension was heated at 50°C for 2 hours, cooled to 0°C and filtered. The solid was washed well with cold DME (ca. 50 ml) and dried under vacuum overnight to yield sodium 2-mercaptobenzoate: 17.6 g (100% yield);

ir, no absorption in the hydroxyl region (3300-3500 cm$^{-1}$) or the carbonyl region (1650-1750$^{cm-1}$).

EXAMPLE VII

To a solution of 15.4 g (0.1 mole) of 2-mercaptobenzoic acid in 20 ml of ethanol was added a solution of 3.8 g (95 moles) of sodium hydroxide in 10 ml of ethanol. The ethanol was removed on a rotary evaporator at 50 mm and the residual solid was triturated several times with ethanol to remove any unreacted 2-mercaptobenzoic acid. The washed solid was dried under vacuum overnight to yield sodium 2-mercaptobenzoate: 10.8 g (61% yield).

EXAMPLE VIII

A solution of methyl 2-mercaptobenzoate (1.7 g, 10 m mol) in 5 ml of anhydrous diethyl ether was slowly added to a stirred suspension of 10 millimoles of sodium hydride in 50 ml of anhydrous diethyl ether, the suspension having been prepared by washing 0.24 grams of a 57% oil dispersion with dry n-hexane (3 times) and replacing the last wash with anhydrous ether (50 ml). The resultant mixture was heated at reflux for 3–4 hours, cooled to 0°C and the green solid removed by filtration and washed well with diethyl ether (ca. 50 ml). The solid was dried under vacuum overnight to yield the sodium salt of methyl 2-mercaptobenzoate: 1.3 g (69% yield):

ir, 3280 (s, broad), 1685 (s) cm$^{-1}$.

nmr, 3.7$\delta$ (3H, s), 6.3–7.4 (4H, complex); no absorption in the 4.5–5.0$\delta$ region.

EXAMPLE IX

A solution of methyl 2-mercaptobenzoate (3.4 g, 20 millimoles) in 5 ml of 1,2-dimethoxyethane (DME) was slowly added, with cooling, to a stirred suspension of 25 millimoles of sodium hydride in DME, the suspension having been prepared by washing 1.1 grams of a 57% oil dispersion with dry n-hexane (3 times) and replacing the last wash with dry 1,2-dimethoxyethane (50 ml). The temperature rose to 40°C during the addition and was then maintained at 40°C for 0.5 hour. The mixture was cooled to 25°C and 3.0 g (21.2 m moles) of methyl iodide was added slowly, during which the temperature rose to 40°C. The resultant mixture was heated at 60°C for 1.0 hour, cooled to 0°C and the excess sodium hydride decomposed by slow dropwise addition of 5 ml of saturated sodium sulfate solution. The mixture was poured into water (100 ml) and neutralized by addition of 20% hydrochloric acid solution. The neutralized mixture was extracted three times with 25 ml portions of methylene chloride and the combined organic extracts were dried over magnesium sulfate, filtered and the solvent removed on a rotary evaporator at 50 mm to yield 2.9 g of pink solid. The solid was recrystallized from n-hexane to yield methyl 2-methylmercaptobenzoate as a white solid: 2.0 g (55% yield); mp 65°–66°C; mol wt 182;

ir, no absorption in the 2500-2600 cm$^{-1}$ region, 1700 (s) cm$^{-1}$.

nmr, 2.4$\delta$ (3H, s), 3.9 (3H, s), 7.0–7.5 (3H, complex), 6.1–8.1 (1H, multiplet).

EXAMPLE X

A solution of 2-mercaptobenzoic acid (15.4 g, 0.1 mol) in 100 ml of 1,2-dimethoxyethane (DME) was slowly added, the cooling, to a stirred suspension of 0.22 mol of sodium hydride in DME, the suspension having been prepared by washing 8.8 grams of a 57% oil dispersion with dry n-hexane (3 times) and replacing the last wash with dry 1,2-dimethoxyethane (250 ml). The temperature was allowed to rise to 45°C during this addition with cooling being applied as necessary to maintain the temperature below 45°C. The resultant green solution was heated at 55°–65°C for 1.0 hour, and then cooled to 25°C. Methyl iodide was added over 10 minutes (15.6 g, 0.11 mole) with enough cooling to maintain the temperature below 40°C. The grey solution was then heated at 40°C for 1.0 hour, cooled to 25°C and neutralized by addition of 35 ml of 20% hydrochloric acid solution. The resulting inorganic salts were dissolved by addition of 75 ml of water.

The resultant aqueous solution was extracted with three 100 ml portions of methylene chloride. The organic extracts were combined, dried over sodium sulfate, filtered and the solvent removed on a rotary evaporator. The residual solid (18.8 g) was recrystallized from a 1:1 mixture of methylene chloride and methanol to yield 2-methylmercaptobenzoic acid as a white solid: 16.4 g (98% yield); mp 168–168.5°C:

ir, 2800-3200 (m, very broad), 1650 (s) cm$^{-1}$.

nmr, 2.4$\delta$ (3H, s), 7.0–7.5 (3H, complex), 7.8–8.1 (1H, multiplet).

EXAMPLE XI

Solution A was prepared by adding 1 gm of methyl 2-mercaptobenzoate to 99 gm of 95% ethyl alcohol. Solution A (0.02 gm) was then added to 100 gm red grape juice (not a Concord variety) to give a level of 2 ppm methyl 2-mercaptobenzoate. This juice sample was compared with the red grap juice without any methyl 2-mercaptobenzoate. The aroma and taste of the juice with the methyl 2-mercaptobenzoate added was described by a bench panel of tasters as more rounded and more Concord grape-like in character than the red juice without any methyl 2-mercaptobenzoate.

Ethyl 2-mercaptobenzoate was tested in the same manner. The red grape juice containing the latter was also described as having more body and being more Concord grape-like than the red juice without any additive.

EXAMPLE XII

A flavoring concentrate of the "Concord grape" type was prepared by admixing the following ingredients:

|  | Parts by Wgt. |
|---|---|
| Methyl anthranilate | 55.0 |
| Ethyl anthranilate | 20.0 |
| Ethyl butyrate | 2.0 |
| Ethyl acetate | 0.4 |
| Triethyl citrate | 15.0 |
| Geranyl acetate | 0.2 |
| Amyl acetate | 0.1 |
| Geranyl propionate | 0.2 |
| Ethyl heptanoate | 2.0 |
| Ethyl oenanthate | 3.5 |
| Ethyl pelargonate | 0.5 |
| Ethyl caproate | 0.2 |
| Alpha ionone | 0.2 |

| | Parts by Wgt. |
|---|---|
| Amyl butyrate | 0.2 |
| Ethyl vanillin | 0.3 |
| Ethyl propionate | 0.2 |
| | 100.0 |

Solution B was prepared by adding 1 gm of the above Concord grape composition to 99 gm of 95% ethyl alcohol.

The "standard" imitation grape flavored drink was prepared by combining 2 grams of solution B, to 120 grams sucrose, 1 gram tartaric acid and 877 grams of water. The "test" imitation grape flavored drink was prepared by adding 0.1 g of solution A, as prepared in Example XI, to the 500 grams of the "standard" drink. The "test" drink differs from the "standard" drink in that the former contains methyl 2-mercaptobenzoate (at a level of 2 ppm).

A flavor panel of five trained flavorists compared the "standard" drink vs the "test" drink. The "test" drink, which contained the methyl 2-mercaptobenzoate was judged as tasting more like the natural fruit juice and being more Concord grape-like in body and character than the "standard" drink.

The same panel compared the "standard" drink with a "test" drink which contained ethyl 2-mercaptobenzoate in place of the methyl 2-mercaptobenzoate. The results were similar in that the "test" drink was judged as being closer in taste to a natural fruit juice, as having more body and as more Concord grape-like than the "standard" drink.

Similar "test" drinks containing 2-mercaptobenzoic acid and its sodium salt (sodium 2-mercaptobenzoate) respectively were described by a bench panel as being more Concord grape-like in character when compared with the "standard" drink.

EXAMPLE XIII

A hard candy mix was prepared by combining:

| | Parts by Wgt. |
|---|---|
| Invert syrup | 55 |
| Corn syrup 42 DE | 170 |
| Sucrose | 335 |
| Water | 150 |

This candy mix was heated to 295°F with stirring and after cooling to 260°F there was added 5 gms citric acid, 2 gms of the solution B (see Example XII) and 0.2 gm of solution A (see Example XI) to provide a "test" candy having about 4 ppm of methyl 2-mercaptobenzoate. An identical composition was also prepared with the omission of solution A and is called the "standard" candy. Tasters stated that a Concord grape juice note was imparted to the hard candy containing the methyl 2-mercaptobenzoate.

Ethyl 2-mercaptobenzoate was also tested under identical conditions and tasters again detected a more rounded, Concord grape juice note than in the hard candy without any additive.

EXAMPLE XIV

A gelatin mix was prepared by combining the following ingredients:

| | Parts by Wgt. |
|---|---|
| Fumaric acid | 2.50 |
| Sodium citrate | 0.85 |
| Sodium chloride | 0.15 |
| Gelatin 275 Bloom | 6.50 |
| Sucrose | 75.00 |
| | 85.00 |

These ingredients were dissolved in hot water and there was added one (1.0) gram of solution B (see Example XII) and 0.1 gram of solution Z (see Example XI) to provide a "test" gelatin having about 2 ppm of methyl 2-mercaptobenzoate. An identical composition was also prepared with the omission of solution A and is referred to as the "standard" gelatin. Tasters stated that the gelatin mix with the methyl 2-mercaptobenzoate had a more natural Concord grape note.

Ethyl 2-mercaptobenzoate was tested under identical conditions. The gelatin containing the latter was described as having more body and being juicier and more Concord grape-like in flavor.

EXAMPLE XV

A chewing gum flavor additive was prepared by admixing the following ingredients:

| | |
|---|---|
| Ethyl acetate | 55.0 |
| Ethyl butyrate | 25.0 |
| Orange oil California | 10.0 |
| Cinnamic aldehyde | 2.0 |
| Ethyl methyl phenyl glycidate | 2.0 |
| Butyl acetate | 6.0 |
| | 100.0 |

A chewing gum mix was prepared by combining:

| | Parts by Wgt. |
|---|---|
| Chewing gum base | 20 |
| Corn syrup 42 D.E. | 20 |
| Confectionery sugar | 60 |

This chewing gum mix (100 g) was heated with stirring to 100°C. Then there was added 1 gm 50% aqueous tartaric acid, 0.5 gms of the flavoring concentrate of "Concord grape" type as prepared in Example XII, 0.5 gms of the chewing gum flavor additive described above and 0.05 gms methyl 2-mercaptobenzoate. An identical composition was also prepared with the omission of the methyl 2-mercaptobenzoate. Tasters unanimously preferred the chewing gum containing the methyl 2-mercaptobenzoate stating that it contained a more rounded flavor, distinctly Concord grape in character. They also stated that the gum without the methyl 2-mercaptobenzoate was fruity, lacked body and was not recognizable as Concord grape in character.

Ethyl 2-mercaptobenzoate was also tested under identical conditions. Tasters stated that the chewing gum containing the ethyl 2-mercaptobenzoate was more Concord grape-like in character.

We claim

1. A method for altering the organoleptic properties of foodstuff which comprises adding thereto an effective amount to impart or enhance Concord grape flavor of a compound of the formula

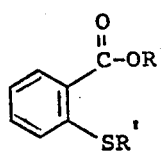

wherein:
R is selected from the group consisting of sodium, hydrogen and an alkyl group of from one to four carbon atoms; and
$R^1$ is selected from the group consisting of hydrogen or sodium when R is an alkyl of from one to four carbons and is hydrogen when R is sodium or hydrogen.

2. The method of claim 1 wherein the effective amount is from 0.1 ppm to 100 ppm of the foodstuff.

3. The method of claim 2 wherein R is methyl or ethyl.

4. The method of claim 3 wherein R' is hydrogen.

5. The method of claim 2 wherein the foodstuff is a grape drink.

6. The method of claim 2 wherein the foodstuff is a candy.

7. The method of claim 2 wherein the foodstuff is a chewing gum.

8. The method of claim 2 wherein the foodstuff is a gelatin.

9. A foodstuff comprising an effective amount to impart or enhance a concord grape flavor of a compound of the formula

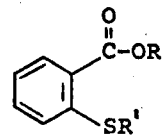

wherein:
R is selected from the group consisting of sodium, hydrogen and an alkyl group of from one to four carbon atoms; and
R' is selected from the group consisting of hydrogen or sodium when R is an alkyl of from one to four carbons and is hydrogen when R is sodium or hydrogen.

10. A foodstuff according to claim 9 wherein R is methyl or ethyl.

* * * * *